US006326523B1

(12) United States Patent
Stahl et al.

(10) Patent No.: US 6,326,523 B1
(45) Date of Patent: Dec. 4, 2001

(54) PROCESS FOR THE DEHYDROGENATION OF A HYDROCARBON FEED STOCK

(75) Inventors: Anni Stahl, Birkerød; Niels Jørgen Blom, Hillerød; Jens Perregaard, Gentofte; Poul Erik Højlund Nielsen, Fredensborg, all of (DK)

(73) Assignee: Haldor Topsøe A/S, Lyngby (DK)

( * ) Notice: Subject to any disclaimer, the term of this patent is extended or adjusted under 35 U.S.C. 154(b) by 0 days.

(21) Appl. No.: 09/536,582

(22) Filed: Mar. 28, 2000

(30) Foreign Application Priority Data

Apr. 12, 1999 (DK) .............................. 1999 00477

(51) Int. Cl.[7] ............................ C07C 5/327; C07C 5/333
(52) U.S. Cl. ..................... 585/654; 585/660; 585/661; 585/662; 585/663
(58) Field of Search ................................ 585/654, 660, 585/661, 662, 663

(56) References Cited

U.S. PATENT DOCUMENTS

| 4,418,237 | 11/1983 | Imai | 585/443 |
|---|---|---|---|
| 4,435,607 | 3/1984 | Imai | 585/443 |
| 4,746,643 | 5/1988 | Buonomo et al. | 502/243 |
| 4,788,371 | 11/1988 | Imai et al. | 585/443 |
| 4,886,928 | 12/1989 | Imai et al. | 585/660 |
| 4,914,075 | 4/1990 | Bricker et al. | 502/330 |
| 5,545,787 | * 8/1996 | Cooper et al. | 585/444 |
| 6,165,352 | * 12/2000 | Cooper et al. | 208/134 |

OTHER PUBLICATIONS

F.P. Wilcher, et al., "Olefin Production by Catalytic Dehydrogenation", 1990 Dewitt Petrochemical Review, Mar. 27–29, 1990; pp. 1–23.

R.O. Dunn, et al., "The Phillips Steam Active Reforming (Star) Process for the Dehydrogenation of $C_3$, $C_4$ and $C_5$ Paraffins", 1992 Dewitt Petrochemical Review, Mar. 25–27, 1992, pp. 1–11.

* cited by examiner

Primary Examiner—Walter D. Griffin
(74) Attorney, Agent, or Firm—Ostrolenk, Faber, Gerb & Soffen, LLP

(57) ABSTRACT

Process for the dehydrogenation of a hydrocarbon feed comprising a step of dehydrogenating the hydrocarbon feed and a step of removing hydrogen being formed by dehydrogenation reactions, wherein the dehydrogenation and hydrogen removal steps are performed simultaneously in presence of a dehydrogenation catalyst being combined with a metal compound being reduced in presence of hydrogen.

4 Claims, No Drawings

PROCESS FOR THE DEHYDROGENATION OF A HYDROCARBON FEED STOCK

FIELD OF THE INVENTION

The present invention relates to a process for dehydrogenation of a hydrocarbon feedstock by contacting the feed at elevated temperature with a dehydrogenation catalyst. More particularly, the invention provides a method for in-situ removal of hydrogen by addition of a metal oxide capable of releasing oxygen at reducing conditions and able to uptake oxygen at oxidation conditions.

PRIOR ART

A number of processes comprising dehydrogenation reactions are known in the art. In general, these processes suffer from a number of disadvantages including low yield of the desired product due to thermodynamic limitation. In addition, the need for addition of large amounts of heat limits the conversion to the desired product. These processes are disclosed in e.g. U.S. Pat. No. 4,914,075; Dunn R. O. et al. (Proceedings, DeWitt Petrochemical Review, Houston, Tex., 1992, 01); Wilcher F. P. et al. (Proceedings, DeWitt Petrochemical Review, Houston, Tex., 1990, T1) and in U.S. Pat. No. 4,746,643.

The known processes for selective removal of hydrogen in a hydrocarbon stream apply a separate stage for the removal of hydrogen. Typically removal of hydrogen is performed by interstage contacting of a partially dehydrogenated stream mixed with oxygen with a noble metal catalyst. Examples of this technology are given in U.S. Pat. Nos. 4,418,237, 4,435,607, 4,788,371 and 4,886,928. The limitation of the above mentioned interstage removal of hydrogen is, besides oxidation of hydrogen in presence of oxygen, it may also effect oxidation of the organic compounds present with formation of carbon dioxide and carbon monoxide as a result. Most dehydrogenation technologies involve at least two steps. A dehydrogenation step where the dehydrogenation catalyst is contacted with a feed of hydrocarbons and a regeneration step where the catalyst is contacted with a feed containing oxygen. Thus, in the dehydrogenation step the reduction potential is high, whereas in the oxidation step the oxidation potential is high.

It is known that many metal oxides are reduced with hydrogen and reoxidised in presence of oxygen at elevated temperature. Such metal oxides are in the following termed redox-oxides. In the above mentioned dehydrogenation cycles these redox-oxides can be reduced in the dehydrogenation step by reaction of metal lattice oxygen with hydrogen forming water, and oxidised in the oxidation step by reaction with oxygen.

By mixing the dehydrogenation catalyst with the redox-oxide and contacting the catalyst and the redox-oxide with a feed containing organic compounds, it is possible to convert organic compound(s) by dehydrogenation reactions that are beyond the known thermodynamic limitation. An example of such application limited to redox-oxide of the perovskites type is given in European Patent Publication No. 558,148 A1.

SUMMARY OF THE INVENTION

In accordance with the above findings this invention is a process for the dehydrogenation of a hydrocarbon feed comprising a step of dehydrogenating the hydrocarbon feed and a step of removing hydrogen being formed by dehydrogenation reactions, wherein the dehydrogenation and hydrogen removal step are performed simultaneously in presence of a dehydrogenation catalyst being combined with a metal compound being reduced in presence of hydrogen.

In the process of the invention, hydrogen, which is formed upon dehydrogenation of organic compound(s), is oxidised by a redox-oxide with high selectivity providing a higher overall conversion and selectivity of the dehydrogenation process. Catalysts being active in the dehydrogenation of hydrocarbon compounds are conventional in the art and known from the literature including the above-mentioned patent publications. In general, any metal compound being able to reversibly change oxidation states at process conditions employed in the process will be useful as a redox metal compound in the inventive process for the removal of formed hydrogen. Those redox metal compounds include oxidic metal compounds, e.g., metal phosphates, and metal oxides, e.g., molybdenum oxide. Preferably, however, a metal phosphate such as vanadium phosphate is used.

The combined dehydrogenation and redox metal catalysts may be prepared by conventional methods known in the art, e.g. physically admixing particles of the dehydrogenation catalyst with the redox metal compound or co-precipitation of the components and optionally with calcination in air.

EXAMPLE 1

A quartz fluid-bed reactor was charged with 100 ml of a dehydrogenation catalyst sample of a chromium-on-alumina catalyst. The catalyst was in form of spheres with an average particle size of 70 $\mu$m.

The reactor was operated at a pressure slightly above atmospheric pressure and in a cyclic mode with the following steps:

1. Oxidation in air at 650° C., 30 min.
2. Purge with nitrogen at 650° C., 15 min.
3. Reduction with CH4 at 650° C., 4 min.
4. Cooling with nitrogen from 650° C. to 580° C., 15 min.
5. Dehydrogenation of i-butane at 550–580° C., 15 min.
6. Purge with nitrogen, 15 min.

Steps 1 to 6 were repeated several times and the temperature in the dehydrogenation step was varied.

As a comparison example, pure dehydrogenation catalyst was used. The feed flow in the dehydrogenation step was 40 Nl/h. The exit gas from both oxidation step and the following purge step was collected in a bag. In a separate bag the exit gas from the dehydrogenation step and the following purge step was collected. The composition of the gas in the two bags was analysed by gas chromatography. The results are given in Table 1.

EXAMPLE 2

After addition of 2% wt of silica coated vanadium phosphorous redox-oxide the tests described under Example 1 were repeated. The results are given in Table 1.

EXAMPLE 3

After addition of 5% wt of silica coated vanadium phosphorous redox-oxide the tests described under Example 1 were repeated. The results are given in Table 1.

TABLE 1 i-butane dehydrogenation

| Experiment | Temperature °C. | Conversion % wt | Selectivity % wt |
|---|---|---|---|
| 1 Pure dehydrogenation | 550 | 41,15 | 91,20 |
| 1 Pure dehydrogenation | 560 | 44,91 | 89,79 |
| 1 Pure dehydrogenation | 570 | 49,48 | 87,14 |
| 1 Pure dehydrogenation | 580 | 54,05 | 83,17 |
| 2 + 2% wt redox-oxide | 550 | 39,57 | 94,30 |
| 2 + 2% wt redox-oxide | 560 | 43,39 | 93,51 |
| 2 + 2% wt redox-oxide | 570 | 47,60 | 92,10 |
| 2 + 2% wt redox-oxide | 580 | 52,13 | 90,18 |
| 2 + 2% wt redox-oxide | 590 | 56,35 | 87,86 |
| 3 + 5% wt redox-oxide | 560 | 39,59 | 93,94 |
| 3 + 5% wt redox-oxide | 570 | 44,70 | 92,87 |
| 3 + 5% wt redox-oxide | 580 | 49,39 | 92,03 |

EXAMPLE 4

A quartz fluid-bed reactor was charged with 100 ml of a dehydrogenation catalyst sample of a chromium-on-alumina catalyst. The catalyst was in form of spheres with an average particle size of 70 μm.

The reactor was operated at a pressure slightly above atmospheric pressure and in a cyclic mode with the following steps oxidation in air at 650° C., 30 min:
1. Purge with nitrogen at 650° C., 15 min.
2. Dehydrogenation of propane at 550–620° C., 15 min.
3. Purge with nitrogen, 15 min.

The steps 1 to 4 were repeated several times and the temperature in the dehydrogenation step was varied.

As a comparison example the pure dehydrogenation catalyst was used. The feed flow in the dehydrogenation step was 52 Nl/h. The exit gas from both oxidation step and the following purge step was collected in a bag. In a separate bag the exit gas from the dehydrogenation step and the following purge step was collected. The composition of the gas in the two bags was analysed by gas chromatography. The results are given in Table 2.

EXAMPLE 5

After addition of 5% wt of silica coated vanadium phosphorous redox-oxide the experiments described under Example 4 were repeated. The results are given in Table 2.

EXAMPLE 6

After addition of 10% wt of silica coated vanadium phosphorous redox-oxide the experiments described under Example 4 were repeated. The results are given in Table 2.

TABLE 2

Propane dehydrogenation

| Experiment | Temperature °C. | Conversion % wt | Selectivity % wt |
|---|---|---|---|
| 4 Pure dehydrogenation | 575 | 45,31 | 63,53 |
| 5 + 5% wt redox-oxide | 575 | 30,80 | 86,12 |
| 5 + 5% wt redox-oxide | 605 | 43,67 | 75,09 |
| 5 + 5% wt redox-oxide | 612 | 46,42 | 73,89 |
| 6 + 10% wt redox-oxide | 612 | 38,59 | 62,52 |

What is claimed is:

1. Process for the dehydrogenation of a hydrocarbon feed, comprising:

dehydrogenating the hydrocarbon feed; and removing hydrogen being formed by the dehydrogenation of the feed, wherein the dehydrogenation and hydrogen removal steps are performed simultaneously in the presence of a dehydrogenation catalyst being combined with a metal phosphate being reduced in the presence of hydrogen.

2. Process of claim 1, wherein the combined metal phosphate and dehydrogenation catalyst is in the form of a physical mixture.

3. Process of claim 1, wherein the combined metal phosphate and dehydrogenation catalyst is obtainable by co-precipitation of corresponding precursor material and thermal treatment.

4. Process of claim 1, wherein the metal phosphate is vanadium phosphate.

* * * * *